US007075652B1

(12) United States Patent
Sarvazyan et al.

(10) Patent No.: US 7,075,652 B1
(45) Date of Patent: Jul. 11, 2006

(54) APPARATUS AND METHOD FOR MEASURING TEMPERATURE DEPENDENT PROPERTIES OF LIQUID

(75) Inventors: Armen P. Sarvazyan, Lambertville, NJ (US); George Eric Plum, Columbus, OH (US)

(73) Assignee: IBET, Inc., Columbus, OH (US)

( * ) Notice: Subject to any disclaimer, the term of this patent is extended or adjusted under 35 U.S.C. 154(b) by 0 days.

(21) Appl. No.: 10/986,272

(22) Filed: Nov. 12, 2004

(51) Int. Cl.
*G01N 21/00* (2006.01)
*G01N 21/64* (2006.01)

(52) U.S. Cl. ............... 356/432; 356/244; 356/246; 250/458.1

(58) Field of Classification Search ........ 356/423–444, 356/244, 246, 319, 408–410; 250/574–575, 250/458, 461 R, 458.1; 364/160, 148
See application file for complete search history.

(56) References Cited

U.S. PATENT DOCUMENTS

| 3,971,630 | A | | 7/1976 | Sandrock | |
|---|---|---|---|---|---|
| 4,180,739 | A | * | 12/1979 | Abu-Shumays | 250/461.1 |
| 4,262,205 | A | * | 4/1981 | Abu-Shumays | 250/458.1 |
| 4,523,097 | A | * | 6/1985 | Allington | 250/458.1 |
| 4,566,807 | A | * | 1/1986 | Koolen | 374/112 |
| 4,676,639 | A | * | 6/1987 | Van Wagenen | 356/246 |
| 4,739,467 | A | * | 4/1988 | Furusawa | 700/28 |
| 5,140,169 | A | * | 8/1992 | Evens et al. | 250/576 |
| 5,173,742 | A | * | 12/1992 | Young | 356/319 |
| 5,183,042 | A | * | 2/1993 | Harjunmaa et al. | 600/309 |
| 5,192,910 | A | | 3/1993 | Hepp | |
| 5,324,956 | A | | 6/1994 | Fagan | |
| 5,455,177 | A | | 10/1995 | Krause | |
| 5,661,558 | A | | 8/1997 | Nogami | |
| 6,049,081 | A | | 4/2000 | Sterling | |
| 6,058,774 | A | * | 5/2000 | Rengshausen | 73/204.24 |
| 6,072,180 | A | | 6/2000 | Kramer | |
| 6,196,046 | B1 | | 3/2001 | Braig | |
| 6,198,949 | B1 | | 3/2001 | Braig | |
| 6,618,144 | B1 | * | 9/2003 | Reed | 356/343 |
| 6,633,771 | B1 | | 10/2003 | Braig | |
| 6,636,753 | B1 | | 10/2003 | Braig | |
| 6,662,030 | B1 | | 12/2003 | Khalil | |
| 6,678,052 | B1 | * | 1/2004 | Hanagandi et al. | 356/440 |
| 6,717,665 | B1 | * | 4/2004 | Wagner et al. | 356/244 |
| 6,731,961 | B1 | | 5/2004 | Braig | |

\* cited by examiner

*Primary Examiner*—Gregory J. Toatley, Jr.
*Assistant Examiner*—Sang H. Nguyen
(74) *Attorney, Agent, or Firm*—Boris Leschinsky (57) ABSTRACT

The present invention relates generally to a method and apparatus for measurement of optical properties of a liquid as a function of temperature. The method and apparatus are based on formation of a stable temperature gradient through the holding cell containing the liquid under study, measurement of the optical property or properties of interest as a function of position, and relating the positions of the optical measurements to the temperature of the studied liquid at that position. In the preferred application, thermal and thermodynamic properties of solutes are obtained.

29 Claims, 8 Drawing Sheets

APPARATUS AND METHOD FOR MEASURING TEMPERATURE DEPENDENT PROPERTIES OF LIQUID

STATEMENT REGARDING FEDERALLY SPONSORED RESEARCH OR DEVELOPMENT

This invention was made with Government Support under GM62692 awarded by the PHS. The Government has certain rights in the invention.

BACKGROUND OF THE INVENTION

The present invention relates generally to measuring temperature dependent properties of liquids. More particularly, the apparatus and methods of the invention describe an apparatus including a liquid containing cell with a predetermined temperature gradient thereacross equipped with an optical means to measure temperature-dependent optical properties of the liquid of interest contained therein.

Calorimetry is a well-known method of evaluating the thermal and thermodynamic properties of liquids. Prior art in calorimetry is well described in numerous textbooks on physics and physical chemistry and in monographs devoted to the subject. When the liquids display favorable optical properties, methods for indirect determination of thermal and thermodynamic properties are known. Several formulations based on the van't Hoff equation for example have been described in the art aiming at extracting thermodynamic information for non-calorimetric observables measured as a function of temperature. The words "observable" and "property" are used interchangeably in this description and have the same meaning. These van't Hoff methods can be advantageously applied to temperature-dependent spectroscopic data.

Liquids present a variety of temperature dependent optical properties. Several nonlimiting examples are discussed herewith. The refractive index of most pure liquids, mixtures and solutions depends on temperature. Further, liquids containing one or more optically active components display temperature dependent birefringence. Liquids comprising or containing chromophores or fluorophores display temperature dependent absorbance or fluorescence properties. The molecular origins of the temperature dependent changes in absorbance or fluorescence spectra of a particular liquid may arise from one or more of several processes. Examples of thermochromic reactions include ligand substitution reactions such as observed when hexaaquacobalt (II) is heated in mixtures of water and primary alcohols. Other examples include temperature dependent changes in ionization state of chromophores or fluorophors, which are coupled to optical changes. Other examples include processes in which molecular complexes change conformation as a function of temperature resulting in changes in optical properties. Such processes frequently involve changes in the solvent exposure of chromophores or fluorophores attached to polymers. Examples include the temperature dependent conformational changes in proteins and nucleic acids which alter the chemical environment of intrinsic (such as amino acid side chains or covalently bound cofactors in proteins or nucleobases in nucleic acids) or extrinsic (such as noncovalently bound cofactors, or drug molecules) chromophores or fluorophores. Macromolecule conformations may be mediated by small molecule effectors as a function of temperature. Such small molecule mediated effects on optical properties are observed frequently with proteins and nucleic acids but may also be observed in synthetic polymers or carbohydrates an example of which is the changes observed when iodine-starch mixtures are subjected to temperature changes. In the above examples, if the chromophore or fluorophore is optically active or bound to an optically active substrate temperature dependent dichroism or anisotropy may be observable.

Current temperature-dependent spectroscopic and calorimetric methods are laborious and material intensive. In most cases, spectroscopic methods require measuring an optical property of a liquid at one particular temperature preset point and then repeating this measurement for another temperature point until the entire characteristic of the optical property is obtained. Complex sample holding cells are described in the prior art allowing maintaining the temperature of the sample liquid at a desired level. An example of such a cell is described in the U.S. Pat. No. 5,192,910 and includes a sophisticated system for maintaining the same temperature throughout the entire liquid volume. A significant amount of time is needed to achieve and stabilize the temperature of the next measurement point and therefore the entire characteristic can not be obtained quickly.

Improvements in sample throughput are therefore needed to make high-throughput thermodynamics practical. A throughput increase of at least two orders of magnitude is required. A need exists in a liquid spectroscopy technology permitting a significant acceleration in optical and thermodynamic characterization of liquids.

Another disadvantage of the temperature dependent optical methods of the prior art is in the discrete nature of measurements. Only certain temperature points are available on the curve and therefore in transitional phases it is quite difficult to obtain information about the property of interest with sufficient resolution without either prior knowledge of the point of transition and its breadth or the time consuming collection of high resolution data outside the range of interest. This also pertains to so-called "zooming", when the property is evaluated most closely and at smallest temperature increments at a temperature from just below to just above the temperature of transition. The need exists therefore for a device and a method of obtaining optical property of the liquid in a way that accounts for all temperature data points continuously or at sufficient resolution to approximate a continuous measurement from a predetermined first temperature to a predetermined second temperature.

The preferred application of the invention is for liquids containing biological macromolecules. The need exists for a device and method allowing rapid characterization of the thermodynamics of biological macromolecule solutes and their interactions. Such characterizations are useful for drug design, design of probe molecules for use in high-throughput screening, protein engineering, and nucleic acid based diagnostics. Further applications of the method and device in proteomics, genomics and material science are anticipated.

SUMMARY OF THE INVENTION

Accordingly, it is an object of the present invention to overcome these and other drawbacks of the prior art by providing a novel apparatus and methods for collecting a temperature profile of a temperature-dependent optical property of a liquid all at once in a novel holding cell with predetermined temperature gradient.

It is another object of the present invention to provide an apparatus and a method for obtaining temperature-dependent melting curve for an optical parameter of a liquid for all temperatures continuously from a first predetermined temperature to a second predetermined temperature.

It is another object of the present invention to provide a device and methods for highly effective measuring temperature-dependent optical properties of liquids within a short period of time to ensure high throughput and productivity of the measurements.

It is a further object of the present invention to provide a sample holding cell with a stable temperature gradient thereacross and with optically transparent windows allowing non-invasive optical interrogation of the liquid of interest.

It is yet a further object of the present invention to provide a sample holding cell with a known temperature profile at any point along its geometry from one end to the other to permit applying a known temperature gradient to a liquid of interest in order to collect continuous data for the desired temperature-dependent optical property of that liquid.

The device and methods of the invention are aimed at evaluating the thermodynamic properties of biological macromolecules and other solution components for which a temperature-dependent transition results in a change in optical properties. The present invention allows collecting an entire thermal melting curve all at once, thereby avoiding several deficiencies of standard methods. This is accomplished by optical examination as a function of position of a solution in a cell designed to produce a stable temperature gradient. The optical observable measured at any position is related easily and directly to the temperature at that position, thereby allowing reconstructing of a thermal melting curve from data collected in a just a few seconds or minutes. The method of the invention speeds the process of data collection up to 100 fold or more. Besides the advantage of greater throughput, the technology of the invention permits conducting of a number of experimental protocols that cannot be accomplished by conventional instrumentation.

The general concept behind the method of the invention is to place a liquid of interest in a holding cell with optically transparent windows designed to establish and maintain a stable temperature gradient across the liquid. The liquid is examined optically as a function of position in the temperature gradient holding cell. The optical observable measured at any position is related easily to the temperature at that position. A thermal melting curve or temperature profile, defined as an optical observable versus temperature, can be obtained from data collected in a just few seconds or minutes along the entire holding cell. The interrogating light may comprise a single wavelength, multiple wavelengths, or a broad band of wavelengths. The optical observable may be measured at one or more specific wavelengths or may comprise a spectrum measured over a range of wavelengths. The optical observable may include but not be limited to absorbance, fluorescence, and refractive index. Use of polarized light permits applications using linear or circular dichroism, birefringence, optical rotary dispersion, or fluorescence anisotropy. The data collected (optical observable versus temperature) may be analyzed for optical properties or in the preferred embodiment used to extract thermal and thermodynamic information about the investigated liquid.

This method also opens up an opportunity to conduct measurements of the temperature dependent optical properties with adaptively changing values of the temperature limits of these measurements.

The invention principally utilizes the linear thermal propagation property of bars made of materials having high thermal conductivity such as many metals. Preferably, one of the three axes of these bars is significantly longer than the other two. When differing amounts of heat are applied or absorbed from the ends of such a bar, a gradient of temperature results. Temperature sensors at the ends of the bar are used for feedback control of the temperatures at the ends of the bar. Because the temperature of the ends of the bar can be controlled precisely, a stable temperature gradient can be maintained from a first temperature at one end to a second temperature at the other end. The temperature at any point in the bar can be related directly to the distances from the two ends and their temperatures. Therefore, the temperature coordinates are mapped directly to spatial coordinates. A cell can therefore be constructed by hollowing of the bar. The temperature of the space within the hollowed bar will be determined by the surrounding material of the bar. Convection is minimized by constructing the device with a large axial ratio; typically with the long axis being about 20 times or more greater than the shorter axes. An optical cell is therefore constructed with two quartz windows that permit ultraviolet and visible light to pass through the cell. The quartz or glass window material is much less thermally conductive than the metal body of the cell; therefore, a temperature gradient can be established and maintained by control of the temperature at the ends of the metal cell body. When the cell is filled with a liquid of interest and the temperature gradient applied, the optical properties of the solution contained therein are readily measured as a function of temperature.

BRIEF DESCRIPTION OF THE DRAWINGS

A more complete appreciation of the subject matter of the present invention and the various advantages thereof can be realized by reference to the following detailed description in which reference is made to the accompanying drawings in which.

DETAILED DESCRIPTION OF THE PREFERRED EMBODIMENTS OF THE INVENTION

A detailed description of the present invention follows with reference to accompanying drawings in which like elements are indicated by like reference letters and numerals.

Figure 1:
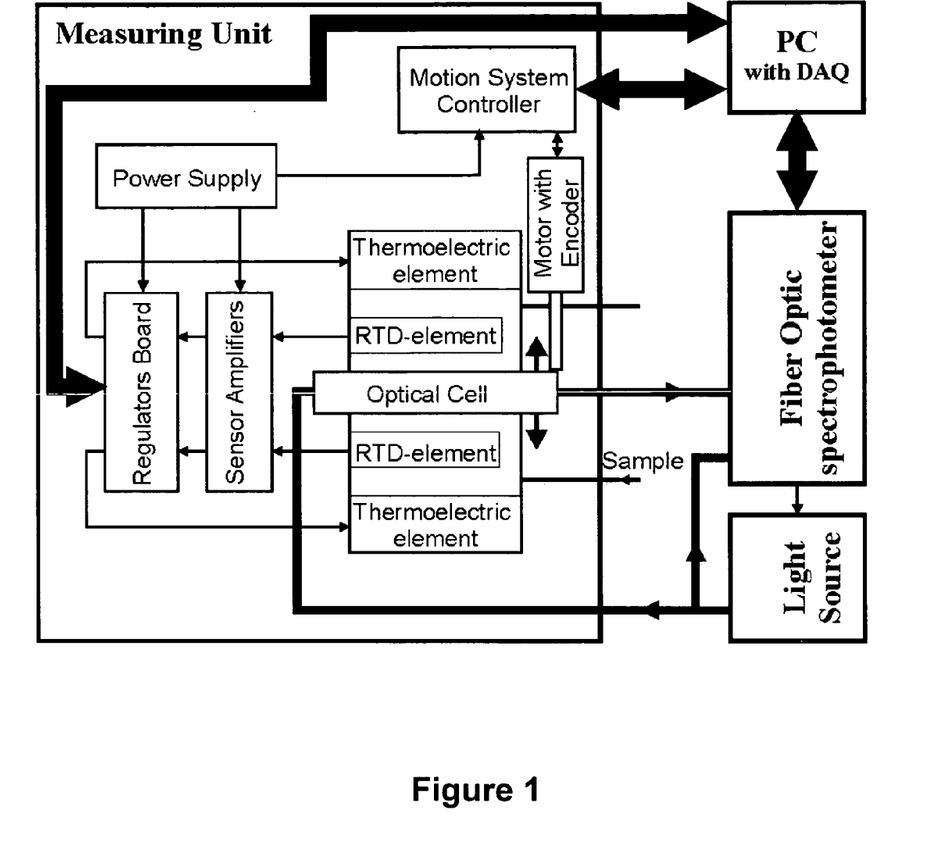
FIG. 1 is a functional schematic of a device of the invention including a temperature gradient holding cell with moving optical fibers interfaced to a commercially available spectrophotometer.

Generally speaking, the device of the invention consists of the following major systems shown on FIG. 1:

A holding cell for containing the liquid of interest,

A temperature control system to create and maintain the desired temperature gradient across the holding cell, An optical system to interrogate the liquid of interest and obtain desired optical properties at one or preferably more points of measurement having a well defined geometrical position relative to the two points defining a temperature gradient across the cell, An optional motion drive positioning system to place the optical system at the desired point along the holding cell (if the optical system can not cover the entire length), and An overall control and data acquisition system such as a personal computer to oversee the entire process automatically and collect data.

Figure 3:
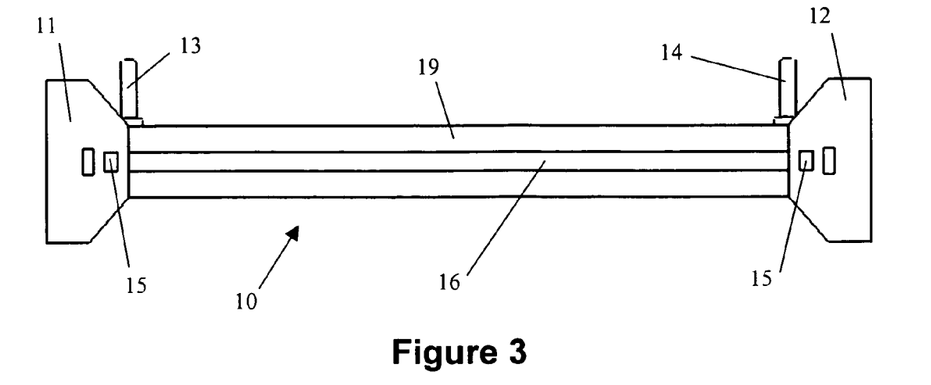
FIG. 3 is a side view of the holding cell of the preferred embodiment of the invention.
Figure 4:
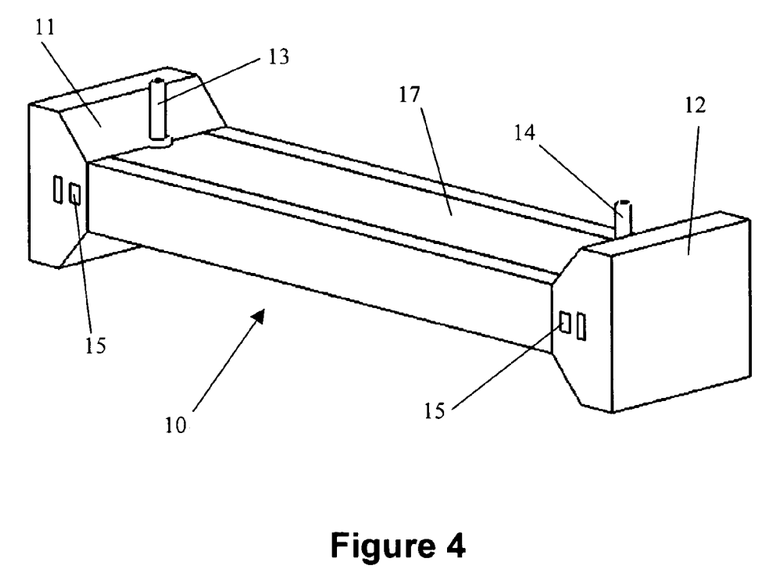
FIG. 4 is a general view of the same with an alternate position of the optical window.

The critical innovative element of the device is the holding cell 10 shown on FIGS. 3 and 4. Its design is based on a predictable temperature conductive property of a rectangular bar made of highly thermo-conductive material such as metal. To be of practical value, the material of the cell should have its thermal conductivity level of at least about 100 W/mK. Gold has high thermal conductivity at about 317 W/mK with 300° K. Another advantage of gold is its chemically non-reactive nature. Copper is another most preferred metal that can be used for making the holding cell due to its known high thermal conductivity of about 401 W/mK. Other preferred metals include silver (429 W/mK), aluminum (237 W/mK) or combinations thereof, optionally covered with a non-reactive coating.

The holding cell 10 is constructed of a single piece of metal or two pieces fused or connected so as to maintain good thermal contact at the ends. The body of the cell 19 extends from a first end 11 to the second end 12. The shape of the ends 11 and 12 is adapted to fit into the temperature control system (described later in detail) so that effective thermal conductivity is obtained. Optically transparent polished quartz windows 16 on the side of the cell (or alternatively on top of the cell as shown on FIG. 4 and depicted as position 17) are incorporated into the cell 10 to form the sample chamber therein. Optional baffling may be used for a specific configuration of the window as shown on top on FIG. 4 to prevent convection. Either thermoplastic cement or a gasket provides the interface between the quartz window and the metal cell body. It is important to match the properties of this material to that of the cell itself to avoid differences in the thermal expansion coefficients for the different materials. To avoid convection in the vertically mounted cell, it is preferred that the cell be mounted exactly vertical and that the opposing sides be exactly parallel. Ports 13 and 14 are included for introduction and removal of liquid solution. Light reference holes 15, one open and one closed, are placed at each end. The fiber optic spectrophotometer requires a measurement through a clear path and a blocked path for calibration of the photo-detector response.

Convection and concomitant redistribution of temperature within the cell are desirably minimized by constructing the device with a large axial ratio; typically with the long axis is made about 20 times or more greater than the shorter axes. It is also preferred to position the cell, strictly vertically and have a higher temperature at the upper end.

The device can be made very small relative to the size of typical spectrophotometer cells used in temperature controlled optical spectroscopy. The entire device can be as small as 10 mm in length, with a height of 0.5 mm and a depth (path length in an absorbance experiment) that can be from 1 to 10 mm. The potential for construction of the device on this small scale opens a number of possibilities for illumination and detection that are not easily realized in larger devices. In addition, the small size of the device permits very rapid thermal equilibration and thus radically reduces the time required for collecting temperature dependent data.

Optionally, other configurations of the holding cell design are contemplated. They include at least one location at which the temperature can be maintained at a predetermined level or adjusted based on a predetermined heating or cooling profile.

In a further variation of the device of the present invention, multiple independent parallel holding cells may be constructed as if from a single block and be controlled by common heating and cooling elements and controller. Alternate window geometries may be constructed to facilitate fluorescence or refractive index measurements. Placing the windows on the top and bottom of the cell would require baffling to prevent convection. A circular arrangement in which the circle is interrupted by the heating and cooling elements may be also employed. In a circular configuration the windows may be arranged such that the optical interrogation is perpendicular to the plane of the circle, or with the light source inside and detector outside the circle, or with the detector inside and light source outside the circle. This configuration will also benefit from baffling to avoid convection.

The material that is in contact with the investigated solution must not interact with it chemically. To prevent interaction of the holding cell body with the solution, the surface of the cell is optionally coated with a non-reactive material. Parylene C (poly(monochloro-p-xylylene)) or a similar polymeric material or gold provides a satisfactory barrier. The Parylene C polymer has a number of favorable properties for the temperature gradient optical holding cell application. It is applied as a gas at ambient temperature by vapor deposition polymerization techniques. This permits thin, uniform coating of irregularly shaped objects. The material melts at 290 C and has excellent water barrier and metal adhesion properties over a wide range of temperatures. Proteins do not stick readily to this material, which is used to coat medical implants, catheters and other medical devices as well as printed electronic circuit boards. The inside of the holding cell also may be coated with a thin layer of gold, which has been used to manufacture high-sensitivity calorimeter cells.

Optionally, two or more optical holding cells can be constructed in a stacked array with common thermoelectric (Peltier) devices and heat sinks. The cells can be illuminated simultaneously as well. The number of cells is not limited. Each of the cells can be filled independently. The body of the apparatus of the invention in that case will have a number of discrete chambers corresponding to the number of cells. A single pair of windows can be used to form two of the sides of each sample chamber with the top and bottom formed by the body of the cell. As with the single chamber cell, gaskets, with gaps corresponding to each chamber or thermoplastic cement is used to seal the window to the body and to relieve stress in the windows. This multiplexing permits several experiments to be conducted simultaneously. For example, a study of the pH dependence of a transition can be completed with one round of cell filling and data collection as opposed to sequential filling, data collection, and cleaning of a single cell device.

The temperature at the center ($T_c$) and the first and second temperatures ($T_l$, $T_u$) at the lower and upper ends of the cell are measured. Due to imperfect insulation of the holding cell from the environment, some (and sometimes significant) deviations of temperature at the center of the cell from that expected for a linear temperature gradient are observed. The magnitude of the nonlinearity depends on the temperature range spanned by the gradient and its relation to the ambient temperature. Because the primary issue is not the linearity of the gradient but its stability, a parabolic approximation based on temperatures measured at the center and at each end of the cell is sufficient to correct for the nonlinearity of the gradient.

The three measured temperatures are used to calculate the temperature at any position x by $$T_x = ax^2 + bx + T_l, \text{ where } a = (T_u - T_l - bL)/L^2, \text{ and } b = (4T_c - 3T_l - T_u)/L, L \text{ is the length of the cell.}$$

Figure 5:
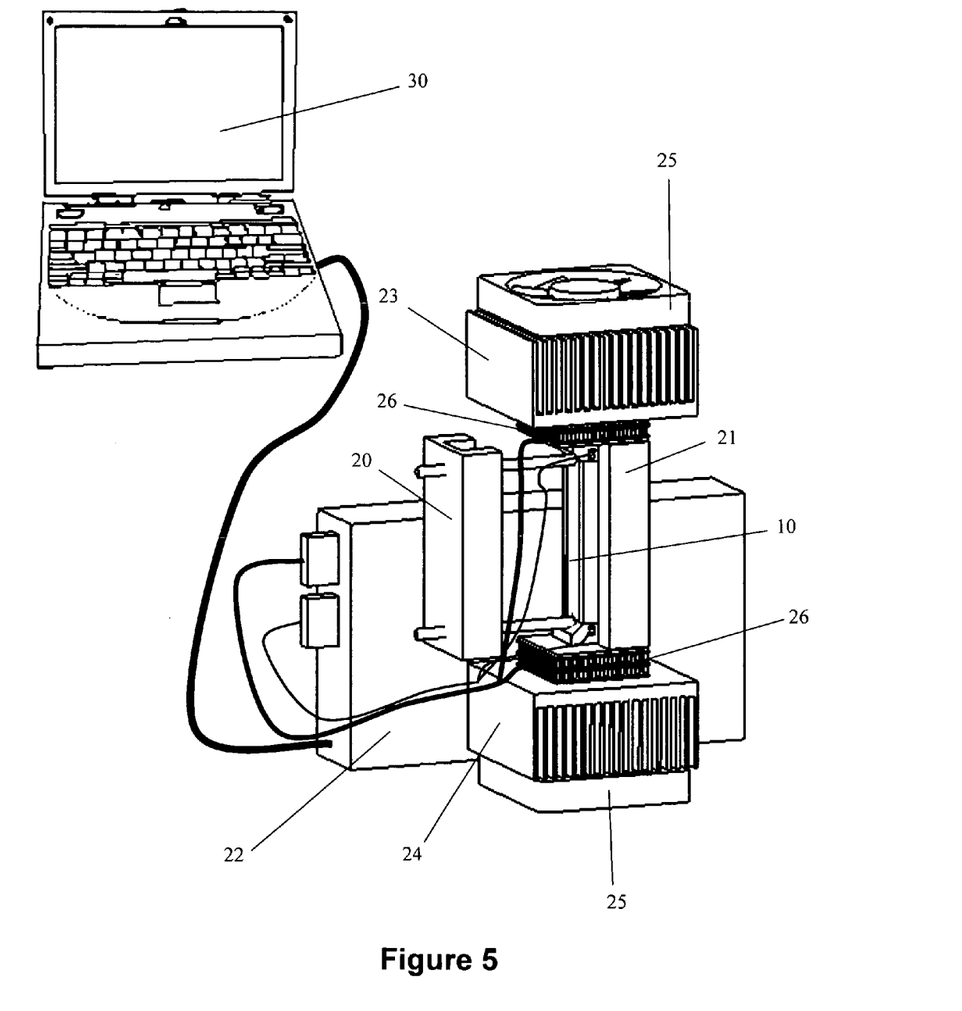
FIG. 5 is a general view of the temperature control system of the invention.

The temperature control system along with the temperature gradient optical holding cell 10 of the invention are shown on FIG. 5. The preferred vertical orientation is shown. The temperature at each end of the cell 10 is controlled independently in a preferred range of between 0 and 100 C. A wider temperature range is also contemplated by using refrigeration systems to cool off one or both ends of the holding cell 10 if needed. Thermal insulation halves 20 and 21 are used to isolate the cell 10 from the environment (FIG. 5 shows one half 20 removed from the cell 10). Multistage Peltier effect thermoelectric elements 23 and 24 provide heating or cooling, as necessary, to the ends of the cell. Other methods of applying heat or cold are also contemplated and include known heaters and coolers. Temperature sensors 26 (such as RTD elements) monitor the temperature at each end of the cell 10. When electrical current is applied to a Peltier element 23 and 24, one surface is heated and the other is cooled. Therefore, heat sinking is critically important to the design. Heat sinking is accomplished by arrays of metal fins and small fans 25 placed at each end of the device or alternately by circulating liquid cooling with a radiator placed away from the temperature gradient holding cell 10. The temperature control unit enclosure 22 contains the power supply, temperature regulation circuitry, and amplifiers for the temperature sensor signals. The temperature set at each end of the cell 10 is determined by an electrical signal originating in the computer 30, which in turn is under software control.

Figure 6:
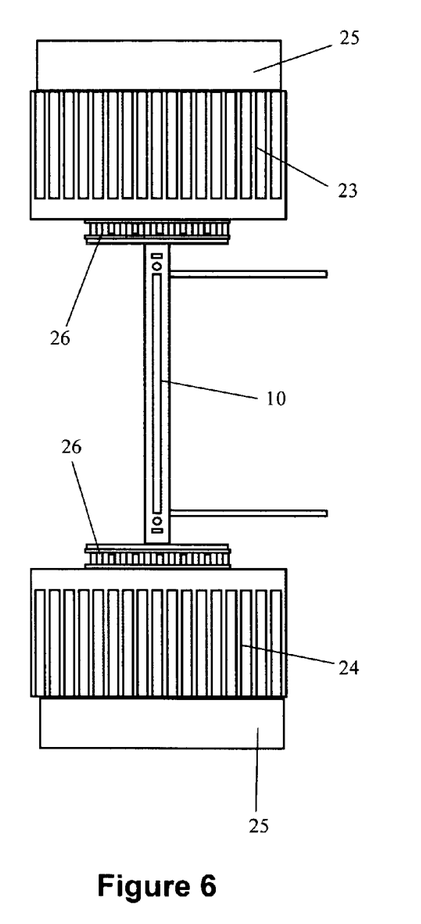
FIG. 6 is a side view of the first configuration of the thermoelectric elements of the invention.
Figure 7:
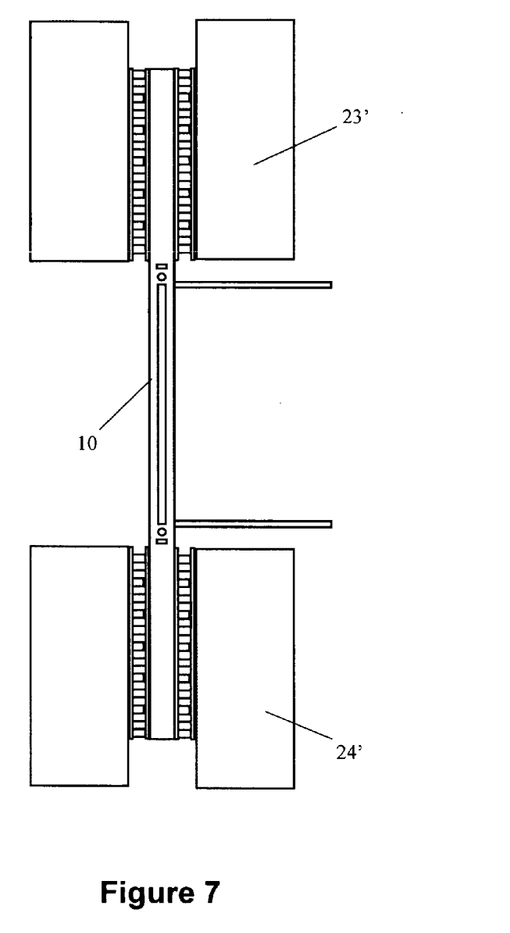
FIG. 7 is a side view of the second alternate configuration of the thermoelectric elements of the invention.

FIG. 6 shows a configuration of the holding cell 10 of the invention with the thermoelectric elements 23 and 24 located across the lower and the upper end of the cell. In an alternate configuration shown on FIG. 7, the thermoelectric elements 23' and 24' are aligned with extended ends of the holding cell 10 to increase the efficiency of heat transfer.

The design of the optical system will now be described in detail. While any optical property can be monitored in a temperature gradient optical holding cell of the invention, the preferred embodiment is a device to monitor absorbance. A commercial fiber optic spectrophotometer permits the measurement of the entire ultraviolet/visible (UV/Vis) absorbance spectrum from approximately 200–800 nm in a fraction of a second. It is comprised of a tungsten/deuterium light source and a self-contained spectrophotometer interconnected by optical fibers 50. The spectrophotometer is interfaced to and controlled by the personal computer 30 shown on FIG. 8.

Figure 8:
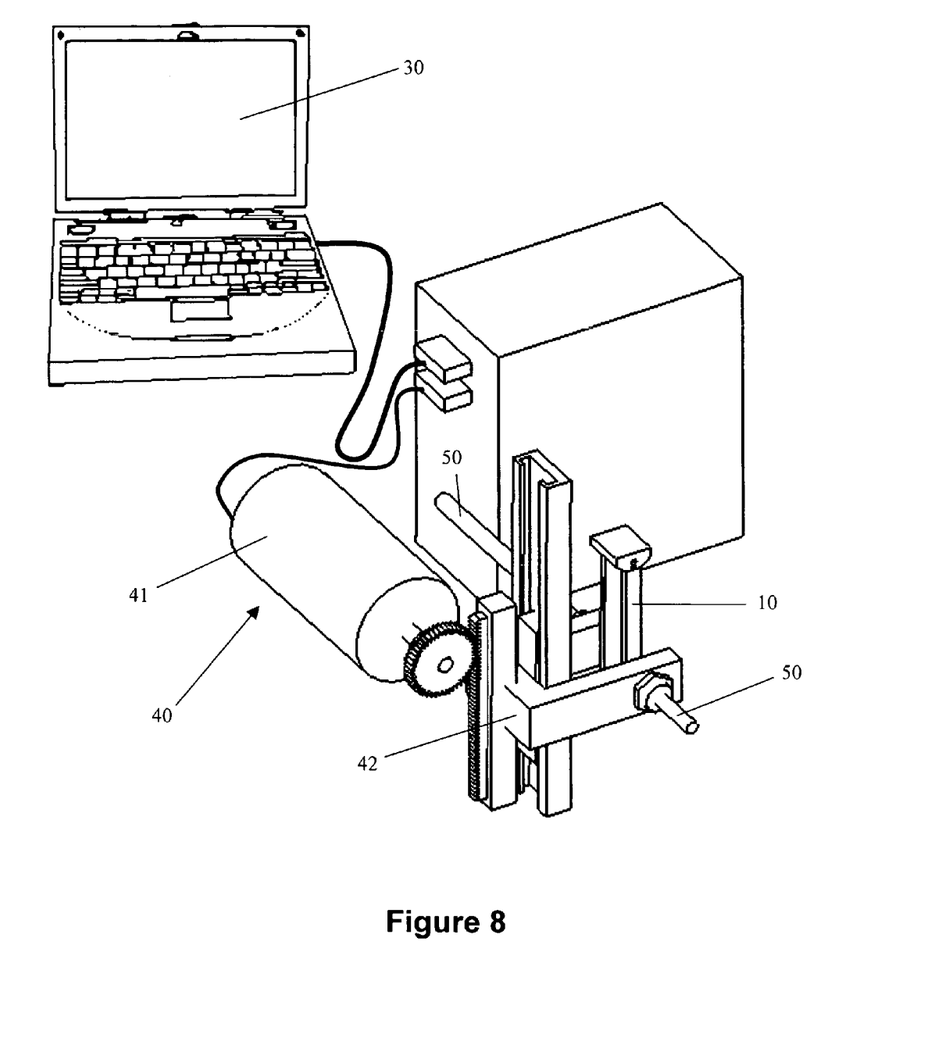
FIG. 8 is a general view of the motion drive system of the invention.

In order to collect absorbance data as a function of temperature, the optical fibers 50 must be aligned and positioned accurately along the length of the optical holding cell 10. Three methods are contemplated to deliver light to the sample cell 10 and to collect the light transmitted through the sample. In the first method, the illuminating and collecting optical fibers of the spectrophotometer are mounted on a "U" shaped stage so they are permanently aligned (FIG. 8). The stage moves so that the temperature gradient holding cell is located between the arms of the "U" shaped stage and the light passes through the cell. A computer-controlled, high-precision, encoded motor 41 and a high-precision, gear-driven, positioning system 42 is forming the motion drive system 40, which is employed to align and move illumination and collection fibers 50 relative to the temperature gradient optical holding cell 10 (see FIG. 8). A computer-controlled motor 41 moves the stage in defined steps parallel to the long axis of the temperature gradient optical cell 10. Spectral data are collected at each step. In this fashion, the entire spectrum is collected as a function of position (and thus temperature) very rapidly relative to a conventional spectrophotometer. A 3-dimensional (absorbance vs. wavelength vs. temperature) melting profile results.

In a second method, an array of illuminating optical fibers may be arranged in fixed position along the length of the cell; a parallel array of collection fibers is aligned to collect light transmitted through the cell. This embodiment allows for simultaneous collection of optical data as a function of position and obviates the requirement to move the optical fibers. The light from the source is preferably focused onto a bundle of optical fibers. The fibers terminate at a linear array of microlenses made of material transparent across the desired illumination spectrum. A second microlens array collects the light that has passed through the sample cell and focuses the light from each lens onto a fiber. With some other types of optical fibers, there is no need for a microlens array and the fibers may be used directly to illuminate and collect the information from the cell. A CCD camera or array of CCD elements images the other end of the collection fiber bundle. Alternatively, the array of collection fibers is omitted and the transmitted light is imaged directly from the cell.

In a further yet configuration of the third method (not shown on the drawings), the optical fibers are fixed in their position and the holding cell 10 is moved along the fibers to allow the collection of required data.

Figure 9:
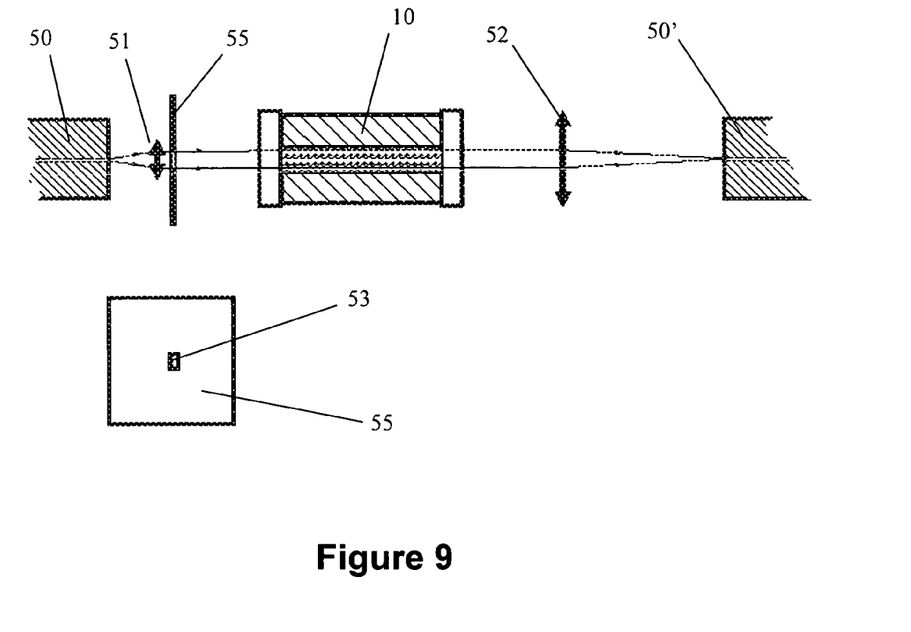
FIG. 9 is a schematic side view of the optical system of the invention.

Several options are available for the illumination system of the holding cell of the invention and the detection of the transmitted light. In all cases, a first lens 51 and a mask 55 are used to collimate the incident light from a fiber 50 and a second lens 52 is used to focus the light transmitted through the sample in the cell 10 onto the end of the collection optical fiber 50', see FIG. 9. A front view of the mask 55 is shown below the diagram indicating a preferred configuration for forming rectangular beam profile through the opening 53. In addition, the optical fiber may be a bundle of optical fibers. In all cases, multiple sample channels can be accommodated although only single channel applications are illustrated herein.

In the simplest embodiment, a band pass filter is used to select a narrow band of incident light. For collecting spectra over a range of wavelengths, a monochromator is used to scan over the desired range of incident light. The light transmitted through the sample is collected and directed to a detector where it is quantified.

Alternatively, the sample containing holding cell can be exposed to the entire light spectrum produced by the lamp with wavelength discrimination subsequent to transmission through the sample. This illumination may occur at a single point along the temperature gradient or over the entire gradient. The device using single point illumination employs a moving stage to position the illumination and collection optical fibers opposite each other straddling the optical path of the cell. The fibers scan the cell parallel to the temperature gradient. The positioning and alignment of the optical fibers relative to the temperature gradient cell is a critical feature of the design. The collected light is directed to a commercial fiber optic spectrophotometer, in which the light is spread by a grating across a linear CCD detector.

The device illuminating the full range of the gradient employs an array of fixed position optical fibers, which illuminate multiple points along the temperature gradient. A parallel array of collection fibers directs the transmitted light to the detector, which is a 1 or 2-dimensional CCD array or camera.

In another embodiment of the device, illuminating the full range of the gradient employs a single collimated light beam shaped to span the length of the temperature gradient.

In a further embodiment of the device, illuminating the full range of the gradient omits the collection fiber array and detects the transmitted light with a 1 or 2-dimensional CCD array or camera.

Another embodiment of the multiple fixed position illumination/collection fiber arrangement directs the transmitted light to strike a grating or prism that displays the diffracted or refracted wavelengths in one direction and the temperature gradient in the other direction on a 2-dimensional detector (CCD array) or camera. Collection of the entire temperature profile spectrum (A vs. λ vs. T) is achieved in one exposure.

As an alternative to CCD detectors, some embodiments may employ photodiode or photodiode array or photomultiplier detection.

Filters or prisms can be used to illuminate the sample with polarized (linearly or circularly) light at some wavelength or set of wavelengths and the absorbance measured. A half-wave plate is interposed between the polarizer and the sample, which reverses the direction of polarization, and again absorbance is measured. The difference between the two-absorbance measurements leads to a value for the dichroism (linear or circular).

Similar to the dichroism measurements, quarter wave plates can be used to measure birefringence or optical rotatory dispersion at selected wavelengths using the temperature gradient refractive index cell technique. Alternatively, refractive index measurements could be made using specialized refractive index sensors and a specially modified rectangular temperature gradient optical cell.

A temperature gradient fluorescence holding cell can be constructed by placement of a third window normal to the incident light, that is, on the side of the cell. The detection occurs normal to the incident beam. A second detector in line with the incident beam, as in the absorbance cell, is included to monitor simultaneously the absorbance of the sample. Here again an array detection scheme is used preferably to collect data from the entire cell simultaneously. An alternative embodiment for fluorescence measurements employs the temperature gradient holding cell designed for absorbance measurements equipped with filters to select for the fluoresced light eliminating the entire transmitted incident light.

In the embodiment for absorbance measurements, the windows in the holding cell have been mounted so as to be parallel. Mounting the windows so that the long sides are at an angle permits the measurement of refractive index, making the cell to behave as a prism.

For light detection and analysis, the use of the fiber optic spectrophotometer has a number of significant advantages. Because a collimated beam of light emerges from the device, the need for elaborate optical design is obviated. The optical problem is reduced to orienting the resultant beam normal to the window of the temperature gradient holding cell, masking of the beam, and alignment of the collecting lens with the beam. This is illustrated in detail on FIG. 9. The mask 55 will permit a narrow beam (e.g. 1 mm high by 0.5 mm) wide to strike the sample. The width of the beam is the determining factor in the temperature resolution of the device.

An integrated software package to control the temperature gradient in the cell, the positioning of the optical fibers were applicable, and the collection, recording, display and analysis of optical property data complete the device.

Figure 10:
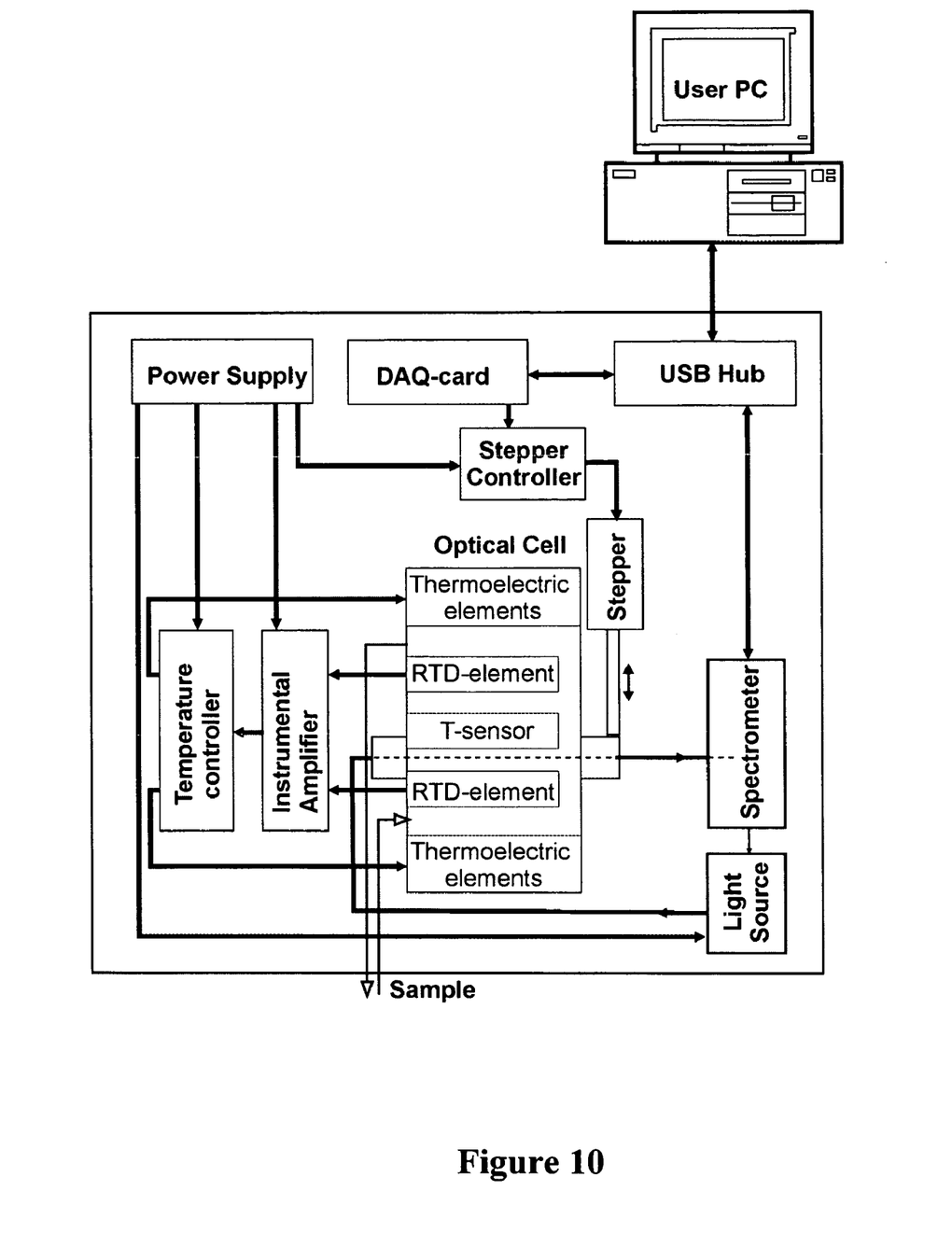
FIG. 10 is a general block-diagram of the alternate configuration of the invention.

The use of a stepper motor is shown on FIG. 10 as an alternate arrangement for the system of the invention.

Figure 11:
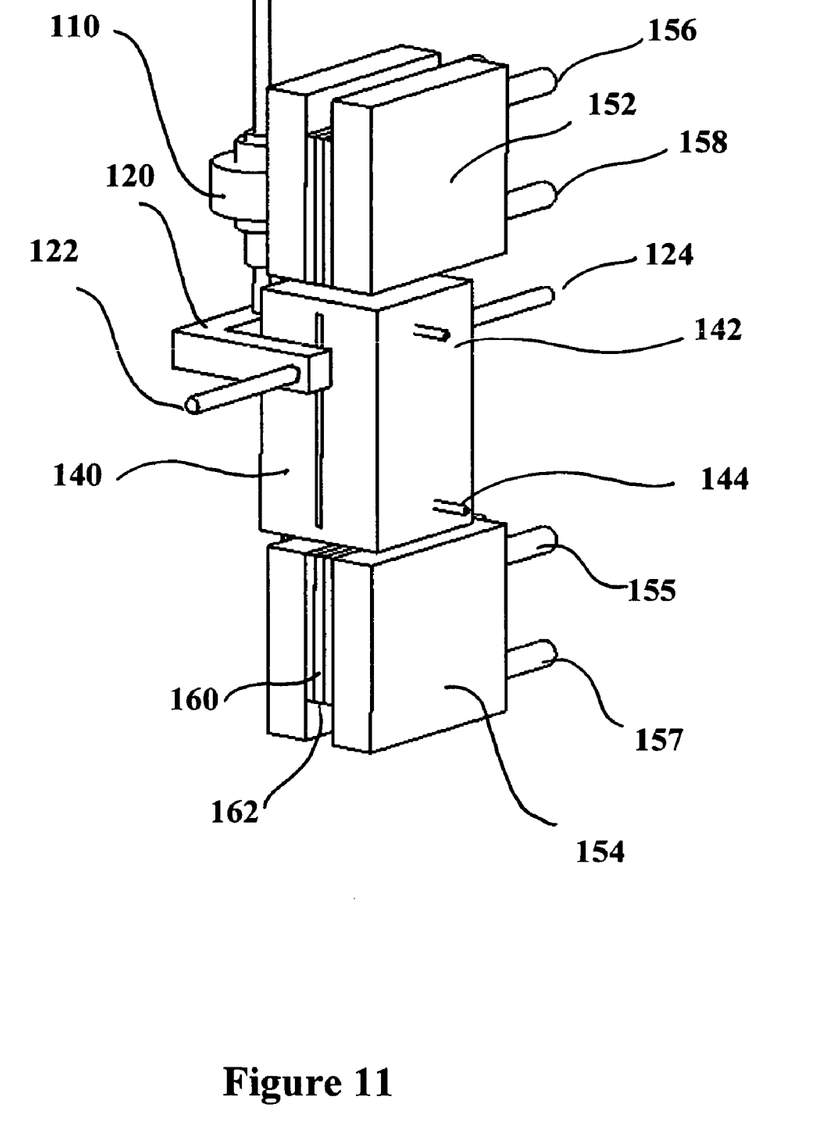
FIG. 11 is a side view of the holding cell and the thermoelectric system of the embodiment shown schematically on FIG. 10.

Another alternate configuration is shown on FIG. 11 and includes a heat shield 140 containing a cell of the invention, which can be filled with liquid of interest through an inlet 142 and emptied through an outlet 144. A U-shaped frame 120, which can be moved up and down by a linear actuator 110, supports the illuminating 122 and receiving 124 optical fibers. The top 152 and the bottom 154 liquid heat exchangers maintain the desired temperature gradient. Hot or cold liquid is circulated through the ports 156 and 158 of the top heat exchanger 152 or through the ports 155 and 157 of the bottom heat exchanger 154. A heat conductor 162 is located in the middle of either heat exchanger and is optionally surrounded by a pair of thermoelectric modules 160 to control its temperature. This version of the device works in a way similar to others as described in more detail above.

Figure 2:
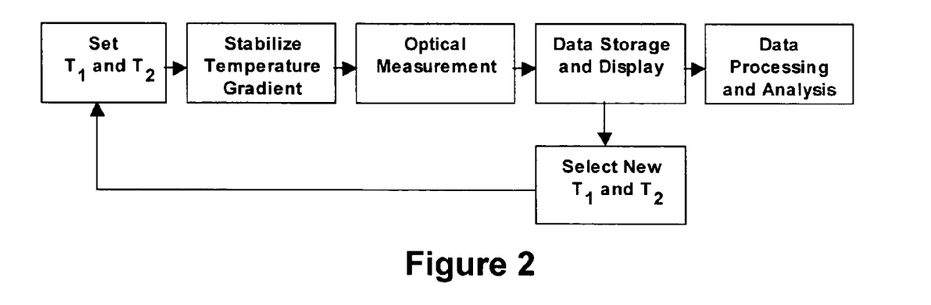
FIG. 2 is a block-diagram of the steps of the basic method of the invention.

In use, the apparatus of the invention provides unique advantages in measuring optical properties of a liquid of interest. A variety of experimental protocols are possible with the apparatus and the methods of the present invention. Common to all of these methods is a basic sequence of steps outlined on FIG. 2. The temperature gradient is defined by the temperatures at the first and second ends of the cell, $T_1$ and $T_2$. The lower temperature is arbitrarily assigned to $T_1$. The temperature gradient is described by $\Delta T = T_2 - T_1$. Note that the temperature resolution varies with $\Delta T$.

By manipulation of $T_1$, $T_2$, and $\Delta T$, a number of unique experiments are possible. The temperatures and all of the spectroscopic measurements are controlled by software on a dedicated personal computer 30. All experiments are variations of a basic procedure: (1) set $T_1$ and $T_2$; (2) wait until temperature gradient is stable; (3) make optical measurements and (4) save data; (5) if experiment is not complete, select new $T_1$ and/or $T_2$ values and return to step 1; (6) analyze the data to extract information on optical properties and/or $T_m$ (the temperature at which the transition is half complete) and thermodynamic parameters of the solution.

Table 1 exhibits unique experiments using the methods of the invention. To collect the same data using a conventional spectrophotometer would in each case require significantly longer time and in some cases a series of distinctly separate experiments.

The experimental protocols are controlled by software. Depending on the experiment, the operator would provide a small number of input parameters, which may include $T_{min}$ and $T_{max}$, the number of steps (number of $T_1$, $T_2$ pairs), the $\Delta T$ value (the breadth of the temperature gradient), $\delta T$ (shift of the window between steps) particular $T_1$ and/or $T_2$ values, or some subset of these. These protocols may be used independently or in combination. The first three experimental methods are deterministic in that the operator defines a set of parameters that are used to define a specific series of temperature windows for data collection. The remaining 3 experimental methods are adaptive in that the breadth of the window and the number of steps are adjusted based on the data recorded for the previous temperature window. In this way, the software can "home in" on the transition region of the temperature gradient. Of these, the adaptive window and zooming window methods must be applied to reversible transitions whereas the zooming window with fixed $T_1$ method can be used for irreversible processes. Assuming that the liquid of interest is similar to water in its dependence of density on temperature, in order to avoid convection with the cell in the vertical orientation, $T_1$ must not exceed the temperature at any point in the cell. Alternately, when there is a need to evaluate water-like liquid at low temperature, the opposite arrangement might be preferred.

TABLE 1

Temperature Gradient Measurement Methods

| Experimental Method | $T_1$ $T_2$ | $\Delta T$ | $\delta T$ |
|---|---|---|---|
| Single Window | $T_{min}$ $T_{max}$ | $T_{max} - T_{min}$ | — |
| Stepping Window, i is the step number | $T_1(i+1) = T_1(i) + \delta T$ $T_2(i+1) = T_2(i) + \delta T$ | const | $\Delta T$ |
| Sliding Window, i is the step number | $T_1(i+1) = T_1(i) + \delta T$ $T_2(i+1) = T_2(i) + \delta T$ | const | $<\Delta T$ |
| Adaptive Window | $T_1(1) = T_{min}$ $T_1(2) = T_2(1)$ $T_1(3) = T_2(2)$ $T_2(1) = T_1(1) + \Delta T(1)$ $T_2(2) = T_2(1) + \Delta T(2)$ $T_1(3) = T_{max}$ | $\Delta T(1)$ = large $\Delta T(2)$ = small $\Delta T(3)$ = large | — |
| Zooming Window | $T_1(1) = T_{min}$ $T_1(2) > T_1(1)$ $T_1(1) = T_{max}$ $T_1(2) = T_1(2) + \Delta T(2)$ | $\Delta T(1) = T_{max} - T_{min}$ $\Delta T(2)$ = small | — |
| Zooming Window with fixed $T_1$ | $T_1(i) = T_1(1), i < n$ $T_1(n) = T_2(n-1)$ | const | — |

$T_1$ and $T_2$ are the set temperatures of the first and second ends of the cell, respectively; $\Delta T = T_2 - T_1$ is the breadth of the temperature window; $\delta T$ the shift in the temperature window between steps, and i is the step number between 0 and n.

For three dimensional equilibrium melting curves analysis, spectra collected as a function of temperature through the thermal melting transition are analyzed by one of several chemometric methods including principle component analysis or singular value decomposition. Singular value decomposition can be used to extract basis spectra, linear combinations of which describe each of the spectra in the temperature profile. The matrix of UV spectra A, is decomposed into a matrix U, of orthogonal basis spectra, a matrix S, in which all of the elements are zero except for the singular values which lie on the diagonal, and a matrix V of coefficients which relate the basis vectors of U to the data matrix A; such that, $A = USV^T$. Examination of the autocorrelation functions of the basis spectra (columns of U) and the coefficient vectors (columns of V) permits one to determine the minimum number of component spectra required to describe the data within the random noise in the spectra. This provides experimental confirmation of one of the primary assumptions of the van't Hoff model; i.e., there are no thermodynamically significant intermediate states. The coefficient vectors, which represent the temperature-induced variation in the absorbance signal integrated over the entire spectral range, can be used to construct melting curves. This provides a melting curve with enhanced signal to noise relative to single wavelength curves. Thermodynamic analysis then proceeds as described in the art.

Although the invention herein has been described with respect to particular embodiments, it is understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. An apparatus for measuring a temperature-dependent optical property of a liquid comprising:
    a first holding cell to contain said liquid, said holding cell defining a first temperature point and a second temperature point,
    a temperature control system adapted to bring a temperature of said first temperature point to and maintain it at a predetermined first temperature level, said temperature control system further adapted to independently and at the same time bring a temperature of said second temperature point to and maintain it at a predetermined second temperature level, whereby defining the difference between said first and said second temperature levels as a temperature gradient between said first temperature point and second temperature point within said holding cell, and
    an optical system adapted to interrogate said liquid contained in said holding cell at a point of measurement and obtain said temperature-dependent optical property, said point of measurement having a known geometrical position relative to said first temperature point and said second temperature point of said holding cell, whereby the temperature of said liquid at said point of measurement is defined by said temperature gradient and said known geometrical position of said point of measurement relative to said first temperature point and said second temperature point of said holding cell.

2. The apparatus as in claim 1, wherein said holding cell having a first end and a second end, said first temperature point located at said first end, said second temperature point located at said second end.

3. The apparatus as in claim 2, wherein said first temperature is greater than said second temperature, said holding cell is oriented vertically such that said first end is located above said second end.

4. The apparatus as in claim 1, wherein said holding cell is made of material with thermal conductivity of at least 100 W/mK.

5. The apparatus as in claim 4, wherein said holding cell is made of a hollowed metal bar.

6. The apparatus as in claim 5, wherein said metal is selected from a group consisting of gold, silver, copper, and aluminum.

7. The apparatus as in claim 5, wherein said hollowed metal bar is covered inside with a non-reactive coating.

8. The apparatus as in claim 7, wherein said non-reactive coating is a Parylene coating.

9. The apparatus as in claim 5, wherein said holding cell defining a long axis and a short axis, said long axis being at least 20 times greater than said short axis.

10. The apparatus as in claim 5, wherein said holding cell containing at least one optically transparent window.

11. The apparatus as in claim 1, wherein said temperature-dependent optical property is selected from a group consisting of absorbance, fluorescence, optical rotatory dispersion at selected wavelengths, circular dichroism, linear dichroism, and refractive index.

12. The apparatus as in claim 1, wherein said temperature gradient between said first temperature point and second temperature point within said holding cell is provided by said temperature control system containing at least one heating and cooling element located at said first temperature point or said second temperature point.

13. The apparatus as in claim 12, wherein said heating and cooling element is a Peltier effect thermoelectric device.

14. The apparatus as in claim 1 further including a second holding cell, said temperature control system including at least one heating and cooling element common to both said first and said second holding cell.

15. The apparatus as in claim 1, wherein said optical system comprising an illumination source located opposite a collection optical fiber across said first holding cell, said collection optical fiber operably connected to a spectrophotometer.

16. The apparatus as in claim 15 further comprising a positioning system equipped with a stage containing said illumination source and said collection optical fiber about said holding cell and in operative relationship thereto, said positioning system adapted to move said stage relative to said holding cell such that said illumination source and said collection optical fiber are placed at said point of measurement of said holding cell across each other.

17. The apparatus as in claim 15, wherein said illumination source including a first lens and a mask to collimate the illumination light, said collection optical fiber includes a second lens to focus said illumination light after passing through said liquid onto the end of said collection optical fiber.

18. The apparatus as in claim 1, wherein said optical system including a plurality of collection optical fibers located at various points of measurement along said holding cell and a common illumination source across therefrom, said plurality of collection optical fibers operably connected to a spectrophotometer.

19. The apparatus as in claim 18, wherein said common illumination source is a plurality of illumination optical fibers located directly across said holding cell from said collection optical fibers.

20. A method for measuring a temperature-dependent optical property of a liquid comprising the steps of:
   a) providing a holding cell containing said liquid, said holding cell defining a first temperature point and a second temperature point,
   b) selecting the values of said first temperature and said second temperature;
   c) bringing a temperature at said first and said second temperature points respectively to said selected first and said second temperature values at the same time by heating or cooling said holding cell at said first and said second temperature points within said holding cell,
   d) illuminating said liquid through said cell with light and collecting said light on the other side of said cell for measuring said temperature-dependent optical property of said liquid at a point of measurement, said point of measurement having a known geometrical position relative to said first temperature point and said second temperature point of said holding cell, and
   e) defining a temperature of said liquid from said first temperature, said second temperature and said known geometrical position of said point of measurement relative to said first temperature point and said second temperature point.

21. The method as in claim 20, wherein said step (c) further including a step of stabilizing a temperature gradient between said first temperature point and said second temperature point.

22. The method as in claim 20 further including a step of selecting new values of said first and said second temperatures and repeating steps (c) through (e).

23. The method as in claim 20 further including steps of data storage and processing and analysis.

24. The method as in claim 20 further including providing a plurality of holding cells and conducting said steps (b) through (e) simultaneously for all holding cells.

25. The method as in claim 20, wherein said step (d) of measuring said temperature-dependent optical properties including a plurality of such measurements at a predetermined number of points of measurement.

26. The method as in claim 20, wherein said step (d) of measuring said temperature-dependent optical property including continuous measurement along the entire holding cell defining a thermal melting curve for said liquid.

27. The method as in claim 20, wherein said step (d) of measuring said temperature-dependent optical property including measurement of said property at various points of measurement simultaneously.

28. The method as in claim 20 further including a step of varying said first or said second temperature using a pre-defined temperature-time profile.

29. The method as in claim 20 further including a step of adaptively changing said first and said second temperatures.

* * * * *